(12) United States Patent
Aboul-Hosn et al.

(10) Patent No.: US 6,814,713 B2
(45) Date of Patent: Nov. 9, 2004

(54) SYSTEMS FOR PERFORMING MINIMALLY INVASIVE CARDIAC MEDICAL PROCEDURES

(75) Inventors: Walid Aboul-Hosn, Fair Oaks, CA (US); Michael DeVries, Fair Oaks, CA (US); Bruce Baker, Placerville, CA (US); William Kanz, Sacramento, CA (US); Jonathan Spangler, San Diego, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 10/132,880

(22) Filed: Apr. 25, 2002

(65) Prior Publication Data

US 2003/0023201 A1 Jan. 30, 2003

Related U.S. Application Data

(60) Provisional application No. 60/286,623, filed on Apr. 25, 2001.

(51) Int. Cl.[7] ............................................. A61M 37/00
(52) U.S. Cl. ....................................... 604/26; 604/107
(58) Field of Search ................. 604/23–26, 39, 604/164.01, 167.01, 167.06, 174, 175, 104, 107, 264

(56) References Cited

U.S. PATENT DOCUMENTS

| | | | |
|---|---|---|---|
| 4,955,856 A | | 9/1990 | Phillips |
| 5,085,635 A | * | 2/1992 | Cragg ................. 604/102.03 |
| 5,613,954 A | * | 3/1997 | Nelson et al. ........ 604/167.03 |
| 5,630,783 A | * | 5/1997 | Steinberg .................... 600/158 |
| 5,741,234 A | | 4/1998 | Aboul-Hosn |
| 5,766,220 A | * | 6/1998 | Moenning .................. 606/213 |
| 6,083,260 A | | 7/2000 | Aboul-Hosn |
| 6,086,570 A | | 7/2000 | Aboul-Hosn et al. |
| 6,113,536 A | | 9/2000 | Aboul-Hosn et al. |
| 6,123,725 A | | 9/2000 | Aboul-Hosn |
| 6,152,704 A | | 11/2000 | Aboul-Hosn et al. |
| 6,210,133 B1 | | 4/2001 | Aboul-Hosn et al. |
| 6,210,397 B1 | | 4/2001 | Aboul-Hosn et al. |
| 6,228,063 B1 | | 5/2001 | Aboul-Hosn |
| 6,234,960 B1 | | 5/2001 | Aboul-Hosn et al. |
| 6,287,319 B1 | | 9/2001 | Aboul-Hosn et al. |
| 6,295,877 B1 | | 10/2001 | Aboul-Hosn et al. |
| 6,395,026 B1 | | 5/2002 | Aboul-Hosn et al. |
| 2002/0111585 A1 | * | 8/2002 | Lafontaine ............ 604/167.06 |
| 2003/0205233 A1 | | 11/2003 | Aboul-Hosn et al. |

FOREIGN PATENT DOCUMENTS

| | | |
|---|---|---|
| WO | WO 99/02204 | 1/1999 |
| WO | WO 99/59652 | 11/1999 |
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 0069489 | 11/2000 |
| WO | WO 01/17581 | 3/2001 |
| WO | WO 01/54749 | 8/2001 |

* cited by examiner

*Primary Examiner*—Loan H. Thanh
(74) *Attorney, Agent, or Firm*—Ryan Kromholz & Manion, S.C.

(57) ABSTRACT

Systems and methods for creating space within the chest cavity to more easily perform minimally invasive cardiac procedures.

3 Claims, 7 Drawing Sheets

SYSTEMS FOR PERFORMING MINIMALLY INVASIVE CARDIAC MEDICAL PROCEDURES

CROSS-REFERENCE TO RELATED APPLICATIONS

This application claims the benefit under Title 35, United States Code, §119(e) of U.S. Provisional Application No. 60/286,623 filed on Apr. 25, 2001 entitled "Systems and Methods for Performing Minimally Invasive Cardiac Medical Procedures."

BACKGROUND OF THE INVENTION

I. Field of the Invention

The present invention relates generally to systems and methods for performing minimally invasive cardiac medical procedures. More particularly, the present invention is directed to systems and methods for creating space within the chest cavity to more easily perform minimally invasive cardiac procedures.

II. Discussion of the Prior Art

Minimally invasive cardiac procedures (otherwise known as "endoscopic" or "closed chest" cardiac procedures) are gaining favor in the medical community for a variety of well-founded reasons. A primary reason for the increasing popularity of such minimally invasive procedures is the significant reduction in trauma to the patient relative to traditional "open chest" procedures, which require a sternotomy to gain access to the heart. The reduction in trauma to the patient translates into shortened periods of hospitalization, which consequently reduces the overall cost associated with such minimally invasive cardiac procedures.

An area of heightened interest is minimally invasive bypass surgery, such as coronary artery bypass graft (CABG) surgery. CABG surgery involves connecting a source of arterial blood downstream from a narrow or occluded section of a coronary artery for the purpose of providing an improved supply of oxygenated blood to the vasculature of the heart. CABG surgery may be performed on a stopped heart or a beating heart. During stopped heart CABG surgery, a full cardiopulmonary bypass (CPB) circuit is employed to divert blood from the lungs for artificial oxygenation at a remote location. This may be referred to as providing "full" cardiac support. During beating heart CABG surgery, it is necessary to provide supplemental circulatory support in order to maintain the hemodynamic stability of the patient. This is preferably accomplished by providing right-heart and/or left-heart assistance, wherein blood is rerouted from one location in the heart to another under the direction of a blood pump so as to obviate the need for an artificial oxygenator, filter, tubing, saline, etc. associated with stopped heart CABG surgery. This may be referred to as providing "partial" cardiac support.

A significant challenge in performing minimally invasive cardiac procedures, such as stopped heart or beating heart CABG surgery, is the lack of space within the chest cavity. More specifically, the chest cavity is constrained in terms of the space available for the surgeon to operate within. This space constraint makes it difficult to manipulate and position the endoscopic instruments, as well as to establish adequate visualization within the chest cavity. The space constraint within the chest cavity thus makes it increasingly challenging for the physician to perform the necessary steps in the given cardiac procedure.

The present invention is directed at eliminating, or at least minimizing the effects of, the above-identified problems.

SUMMARY OF THE INVENTION

The present invention incorporates a multitude of embodiments which enable the introduction of insufflation fluid (gas or liquid) into the chest cavity for the purposes of creating additional space within the chest cavity to facilitate the performance of any of a variety of minimally invasive cardiac medical procedures. In one embodiment, the insufflation system is an access port incorporating a separate insufflation port through which insufflation fluids may be introduced to pressurize the chest cavity while the access port is employed to introduce instruments for performing the minimally invasive cardiac procedure. In a second embodiment, the access port has an elongated body capable of being introduced into an organ disposed within the chest cavity (including but not limited to the heart and associated vasculature), wherein the body includes a separate insufflation port through which insufflation fluid may be introduced into the chest cavity. Contemplated within this embodiment is a variation wherein the body of the access port can be made of a synthetic graft material (with or without an insufflation lumen) capable of being sealed and severed near the proximal region (following use) and subsequently pushed into the chest cavity (leaving the distal region sealed within the organ) for later removal and use should repeat procedures require accessing the internal organ. A third main insufflation device according to the present invention involves equipping a minimally invasive coaxial cannula assembly with a separate insufflation port for introducing insufflation fluid into the chest cavity while the cannula assembly is used within the heart to augment or replace the heart's own beating function. This feature of augmenting or replacing the heart's own beating function during the insufflation of the chest cavity is a significant aspect of the present invention in that it provides the ability to counteract or overcome the heart's diminished pumping ability (particularly on the thin-walled right side of the heart) due to any collapse of the heart chambers or associated vasculature which stems from insufflating the chest cavity. In this regard, a peripheral access coaxial cannula assembly may be similarly employed to augment or replace the heart's own beating function. In both cases, the cardiac output of the heart is maintained. In the context of right heart support during beating heart surgery, both coaxial cannulation systems also serve to reroute blood past the right ventricle. This rerouting past the right ventricle effectively empties the right ventricle, providing yet another space creating mechanism within the chest cavity.

DESCRIPTION OF THE PREFERRED EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of minimally invasive CABG surgery, the chest-cavity-space-creation (CCSC) systems of the present invention may be employed in any number of cardiac procedures. The CCSC systems disclosed herein boast a variety of inventive features and components that warrant patent protection, both individually and in combination.

Figure 1:
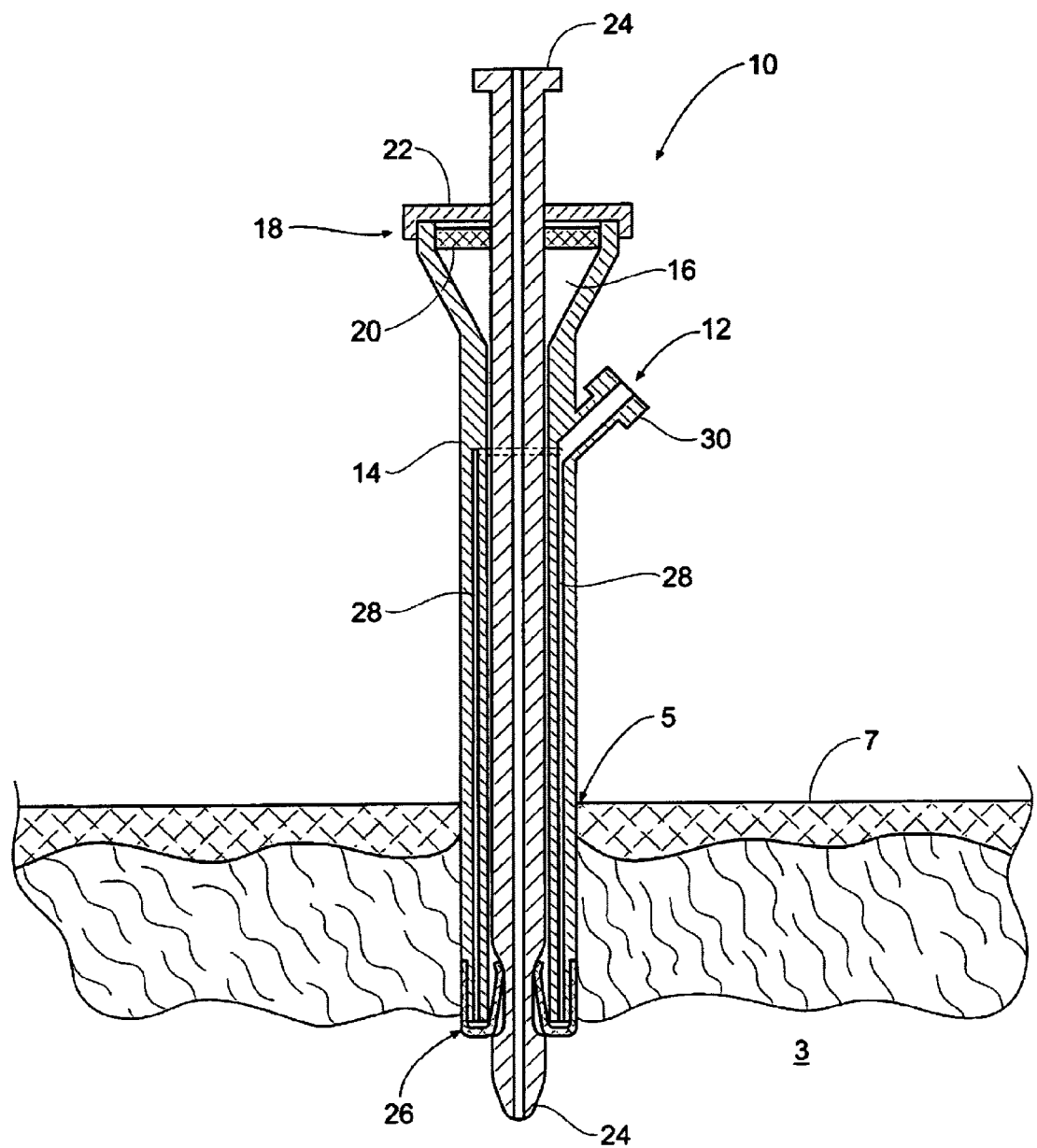
FIG. 1 is a partial cross-sectional view of a chest cavity insufflation device provided in accordance with a first broad aspect of the present invention during insertion into the chest cavity.

Referring initially to FIG. 1, shown is a CCSC system according to a first broad aspect of the present invention. The CCSC system of this embodiment comprises an anatomical cavity access conduit 10 of the type shown and described in commonly assigned and co-pending U.S. patent app. Ser. No. 08/956,654 (now U.S. Pat. No. 6,228,063), the contents of which are hereby expressly incorporated by reference. The access conduit 10 includes a generally cylindrical member 14 having a centrally located access lumen 16. In accordance with the present invention, the anatomical cavity access conduit 10 includes an insufflation port 12 for creating space within the chest cavity 3. The proximal region of the cylindrical member 14 is equipped with a valve assembly 18. By way of example only, the valve assembly 18 includes a seal element 20 and a cap member 22, each dimensioned to slideably pass a penetrating rod 24 therethrough for the purpose of selectively deploying an annular sealing flange structure 26 extending from the distal region of the cylindrical member 14. The seal element 20 serves to prevent the ingress of contaminants into the chest cavity 3 and egress of fluids from the chest cavity 3. The insufflation port 12 is communicatively coupled to one or more insufflation lumen(s) 28 extending within the wall of the cylindrical member 14. As will be explained in greater detail below, the insufflation lumens 28 extend to the distal most region of the cylindrical member 14 such that they open into the chest cavity 3 once the sealing flange structure 26 has been deployed. The insufflation port 12 may include a coupling device 30 (such as a Luer-type fitting) for establishing fluid communication with a source of insufflation fluid.

The sealing conduit 10 of this embodiment is dimensioned to be introduced into the chest cavity 3 through an aperture 5 formed in the chest wall 7. The sealing conduit 10 may be constructed from any number of biocompatible materials suitable for medical use, including but not limited to polymeric material or stainless steel. The central lumen 16 preferably is circular in cross section and has a sufficient diameter to receive different sizes of surgical and diagnostic instruments to be used at an operative site in the body. Although shown having a generally tubular shape, it is to be readily understood that the cylindrical member 14 may be non-tubular in configuration.

Figure 2:
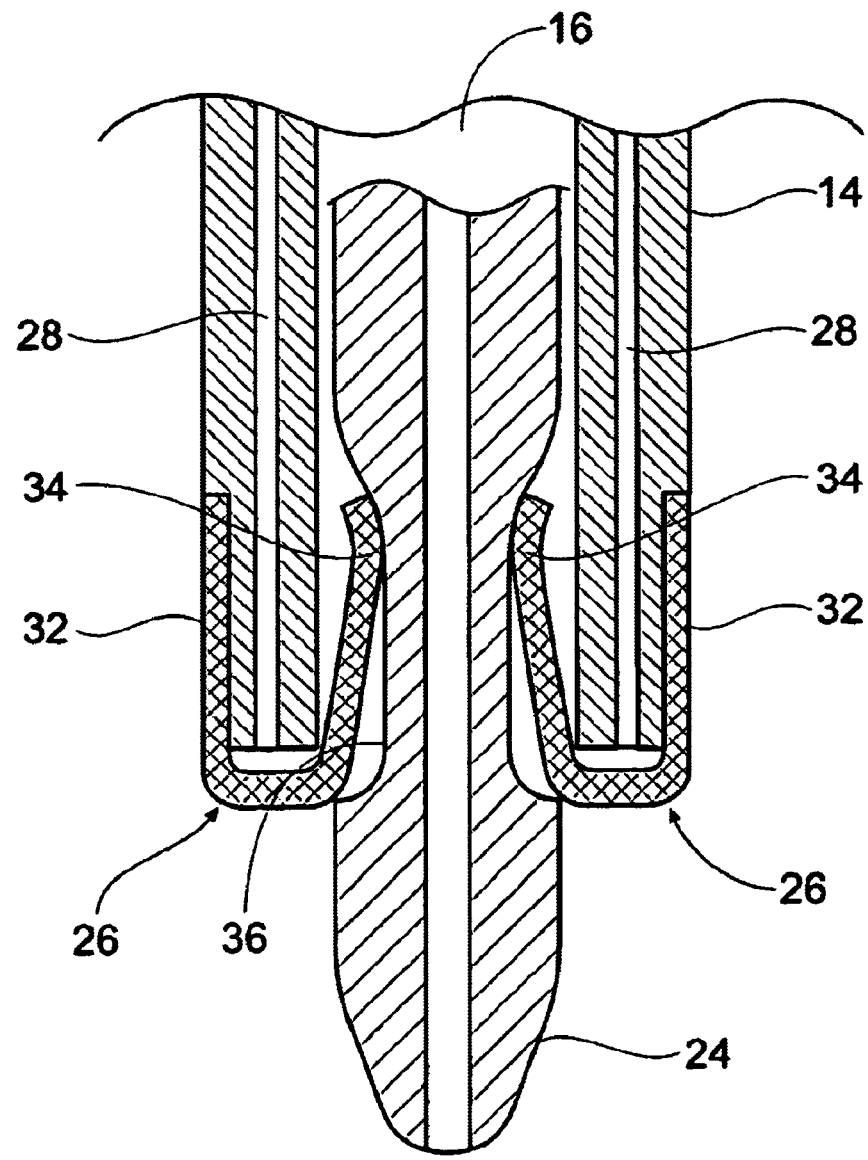
FIG. 2 is an enlarged partial cross-sectional view of the distal region of the chest cavity insufflation device shown in FIG. 1.
Figure 3:
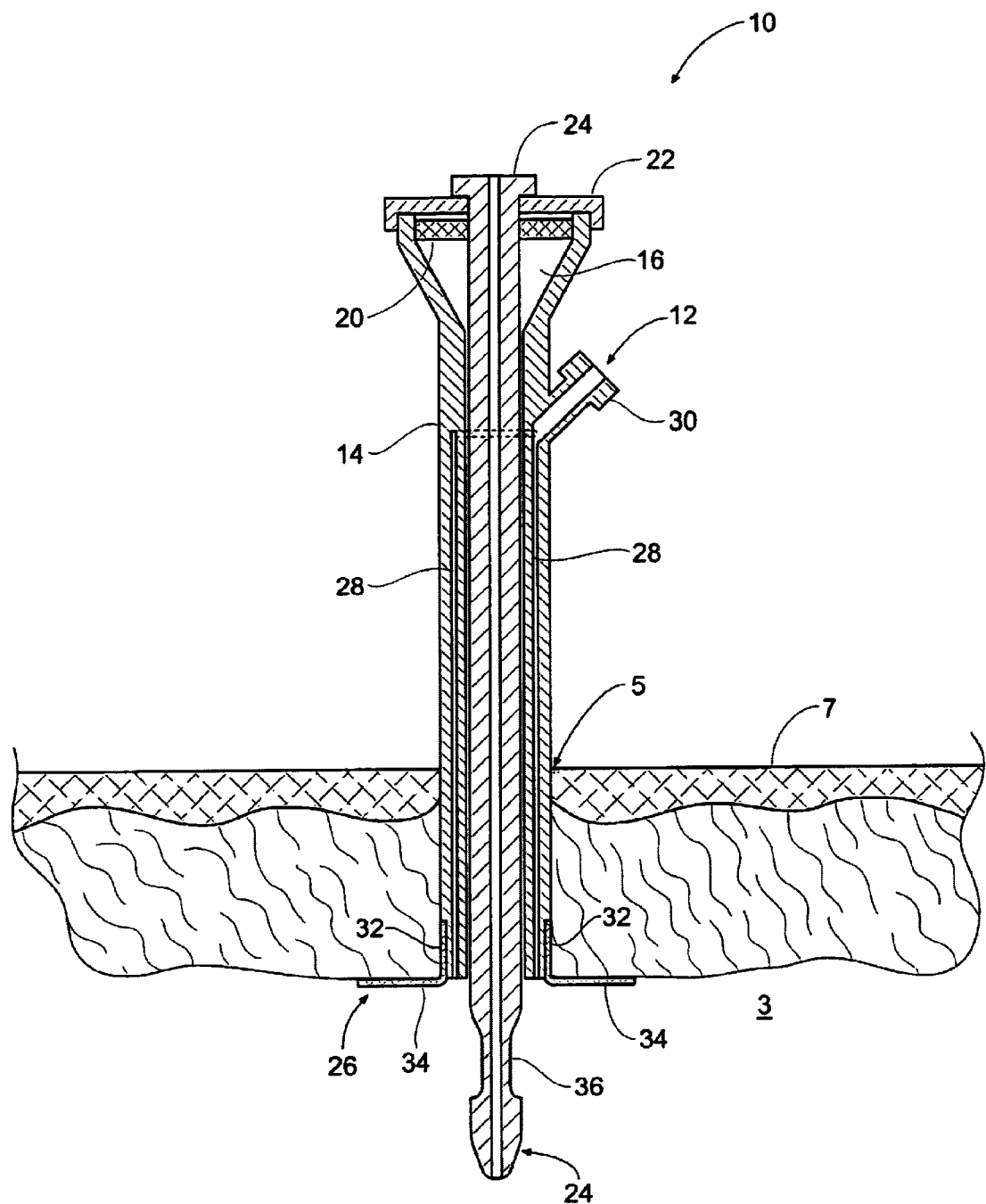
FIG. 3 is a partial cross-sectional view of the chest cavity insufflation device of FIG. 1 following insertion into the chest cavity.

As further detailed in FIG. 2, the annular flange structure 26 includes a neck portion 32 and a flange portion 34. The neck portion 32 and flange portion 34 are preferably of integral, unibody construction. The flange portion 34 is preferably made of a suitably flexible polymeric material biased such that the flange portion 34 may be folded into the lumen 16 during introduction into the chest cavity 3 (FIGS. 1 and 2) and subsequently deployed after introduction into a generally extended fashion (FIG. 3). The penetrating member 24 includes a recessed region 36 dimensioned to receive the flange portion 34 when folded within the lumen 16. The recessed region 36 also serves to force the flange portion 34 out the distal end of the lumen 16 as the penetrating member 24 is slideably advanced through the cylindrical member 14. In a preferred embodiment, the flange portion 34 is biased such that it automatically assumes the position shown in FIG. 3 after it is forced out of the distal end of the cylindrical member 14. In so doing, the generally flat upper surface of the flange portion 34 is pressed against the inside surface of the chest cavity 3 adjacent to the portal 5, thus forming a seal for preventing unwanted ingress or egress into or out of the chest cavity 3 alongside the outside surface of the cylindrical member 14. The penetrating member 24 may then be removed from the cylindrical member 14, thereby availing the lumen 16 such that endoscopic instruments may be advanced therethrough and introduced into the chest cavity 3 for performing cardiac medical procedures.

In an important aspect of the present invention, the insufflation port 12 may then be used to introduce insufflation fluid into the chest cavity 3 for the purposes of creating space therein to facilitate the cardiac medical procedure. As shown in FIG. 3, after the flange portion 34 has been deployed, the distal ends of the insufflation lumens 28 are in fluid communication with the interior of the chest cavity 3. Insufflation fluid (which may be liquid or gas) may be introduced in a fashion such that the chest cavity is pressurized anywhere in the range of between 0 and 300 mm Hg. The liquid may comprise any suitable physiologic fluid having preferably isotonic characteristics, including but not limited to saline. The gas may comprise any suitable inert gas, including but not limited to carbon dioxide. In yet another aspect of the present invention, the insufflation fluid may be provided having a temperature sufficiently lower than that of the human body (98.6 Degrees F.) so as to have a cooling or hypothermic effect on the internal organs. This, in turn, produces various advantageous results, including but not limited to slowing the blood flow within, and cardiac needs of, such organs during surgery.

The advantages of the foregoing embodiment are equally applicable to those that follow, and consequently certain common elements may not be reiterated below.

Figure 4:
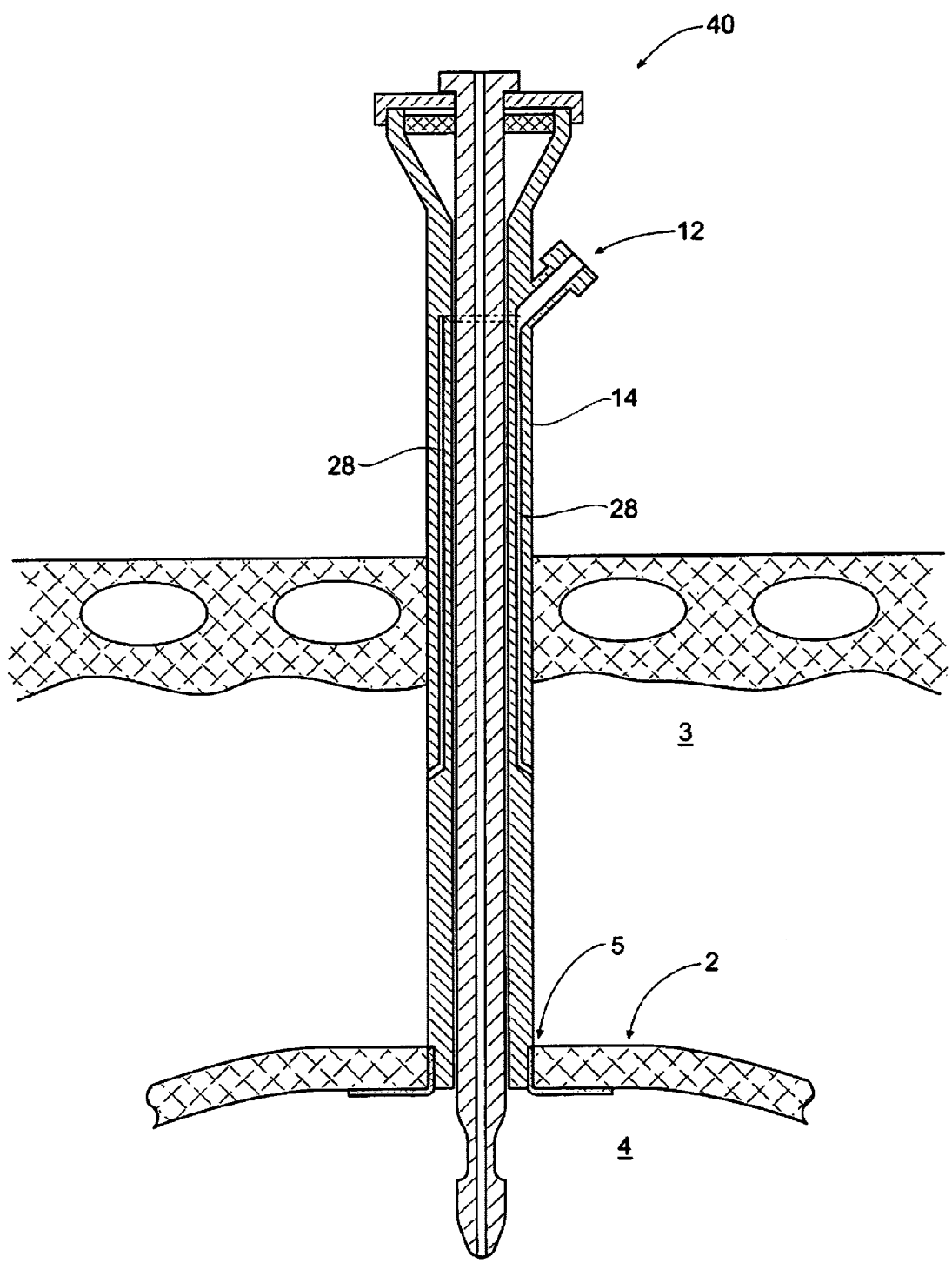
FIG. 4 is a partial cross-sectional view of a chest cavity insufflation device provided in accordance with a second broad aspect of the present invention.

FIG. 4 illustrates an insufflation device similar to that shown in FIG. 1, with the exception that the access port 40 has an elongated body 14 capable of being introduced into an organ 2 disposed within the chest cavity 3. In accordance with the present invention, the organ 2 may include, but is not necessarily limited to, the heart and associated vasculature such as the pulmonazy artery or aorta. As with the embodiment of FIG. 1, the body 14 includes a separate insufflation port 12 through which insufflation fluid may be introduced into the chest cavity 3. Contemplated within this embodiment is a variation wherein the body 14 of the access port 40 can be made of a synthetic graft matexial (with or without an insufflation lumen), wherein the graft material may be sealed and severed near the proximal region following use and subsequently pushed into the chest cavity 3 (leaving the distal region sealed within the port 5 formed in the organ 2) for later removal and use should repeat procedures require accessing the internal organ 2.

Figure 5:
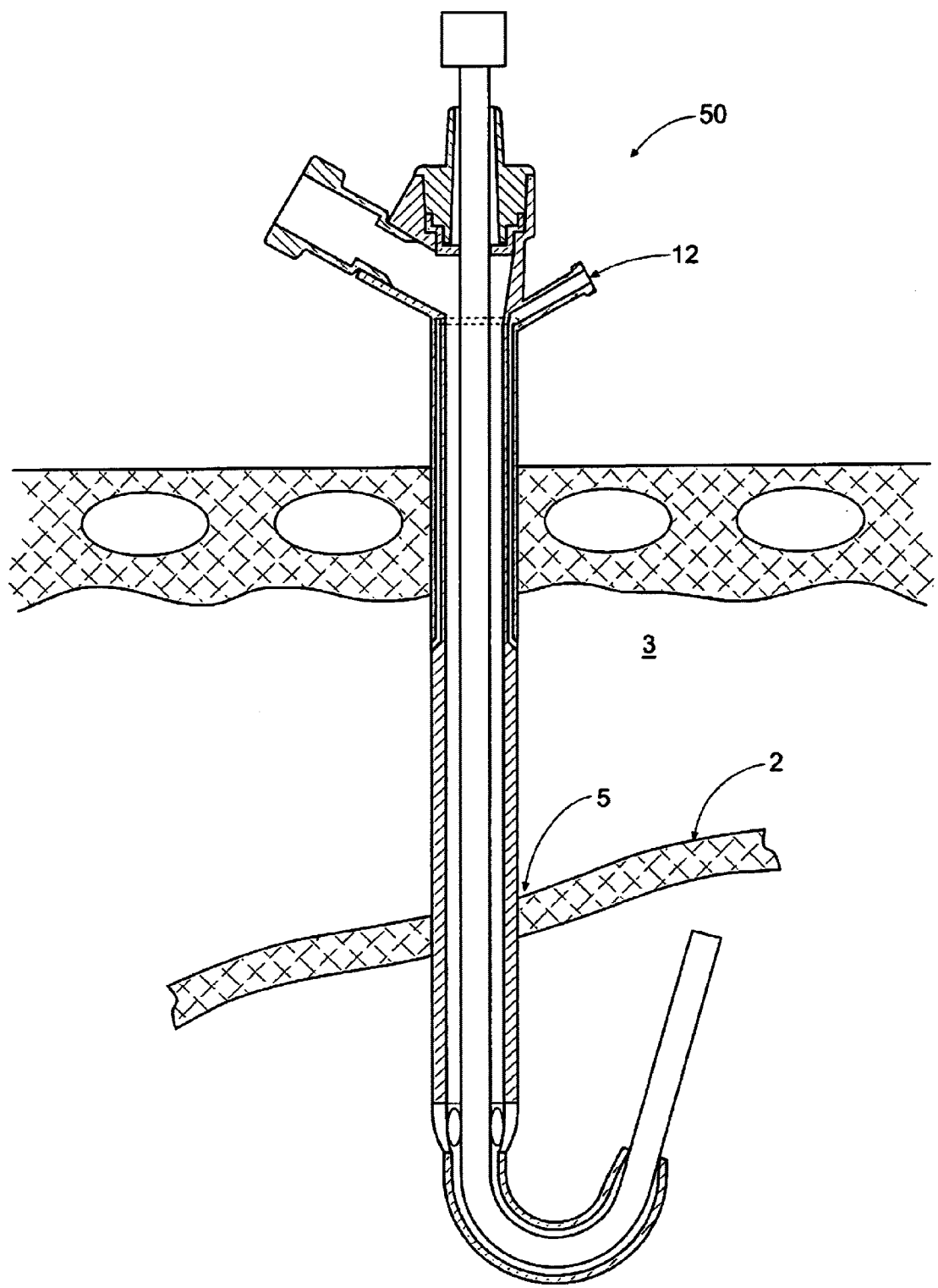
FIG. 5 is a partial cross-sectional view of a chest cavity insufflation device provided in accordance with a third broad aspect of the present invention.

FIG. 5 illustrates a third main insufflation device according to the present invention involves equipping a minimally invasive coaxial cannula assembly 50 with a separate insufflation port 12 for introducing insufflation fluid into the chest cavity 3 while the cannula assembly 50 is used within the heart 2 to augment or replace the heart's own beating function. (The cannula assembly 50 is similar to that shown in commonly owned and copending PCT Application No. PCT/US01/02531 entitled "Cannulation System and Related Methods," the contents of which are incorporated herein by reference.) This feature of augmenting or replacing the heart's own beating function during the insufflation of the chest cavity 3 is a significant aspect of the present invention in that it provides the ability to counteract or overcome the heart's diminished pumping ability (particularly on the thin-walled right side of the heart) due to any collapse of the heart chambers or associated vasculature which stems from insufflation the chest cavity.

Figure 6:
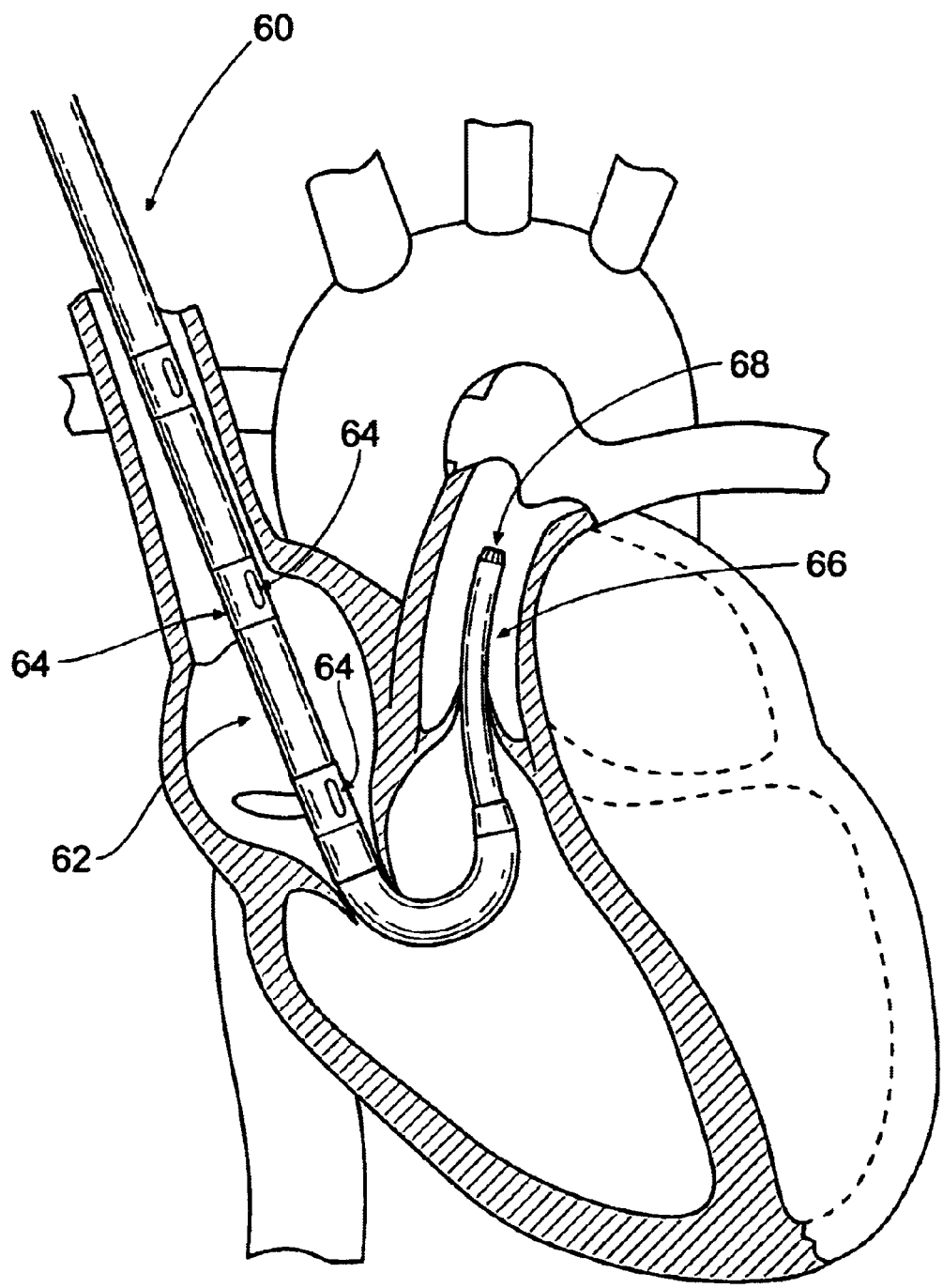
FIG. 6 is a partial cross-sectional view of a chest-cavity-space-creation device (right heart support device) provided in accordance with a fourth broad aspect of the present invention.

According to still further aspects of the present invention, the chest-cavity-space-creation feature may be accomplished or augmented via intravascular cannulation systems capable of providing right and/or left heart support during beating heart surgery. FIG. 6 illustrates one such intravascular cannula system comprising a peripheral access coaxial cannula assembly 60 capable of being employed to augment or replace the heart's right heart beating function during insufflation of the chest 3. The peripheral access cannula system 60 is similar to that shown in commonly owned and copending PCT Application No. PCT/US99/19537 entitled "Intravascular Cannulation Apparatus And Methods of Use," the contents of which are hereby incorporated by reference. The peripheral access cannula system 60 includes an outer cannula 62 having a series of flow ports 64, an inner cannula 66 slideably disposed within the outer cannula 62 and including a distal flow port 68, and a blood pump (not shown) capable of withdrawing blood from the right atrium (via flow ports 64 of outer cannula 62) and rerouting the blood into the pulmonary artery (via flow port 68 of inner cannula 66). This rerouting past the right ventricle effectively empties or unloads the right ventricle, providing yet another space creating mechanism within the chest cavity.

Figure 7:
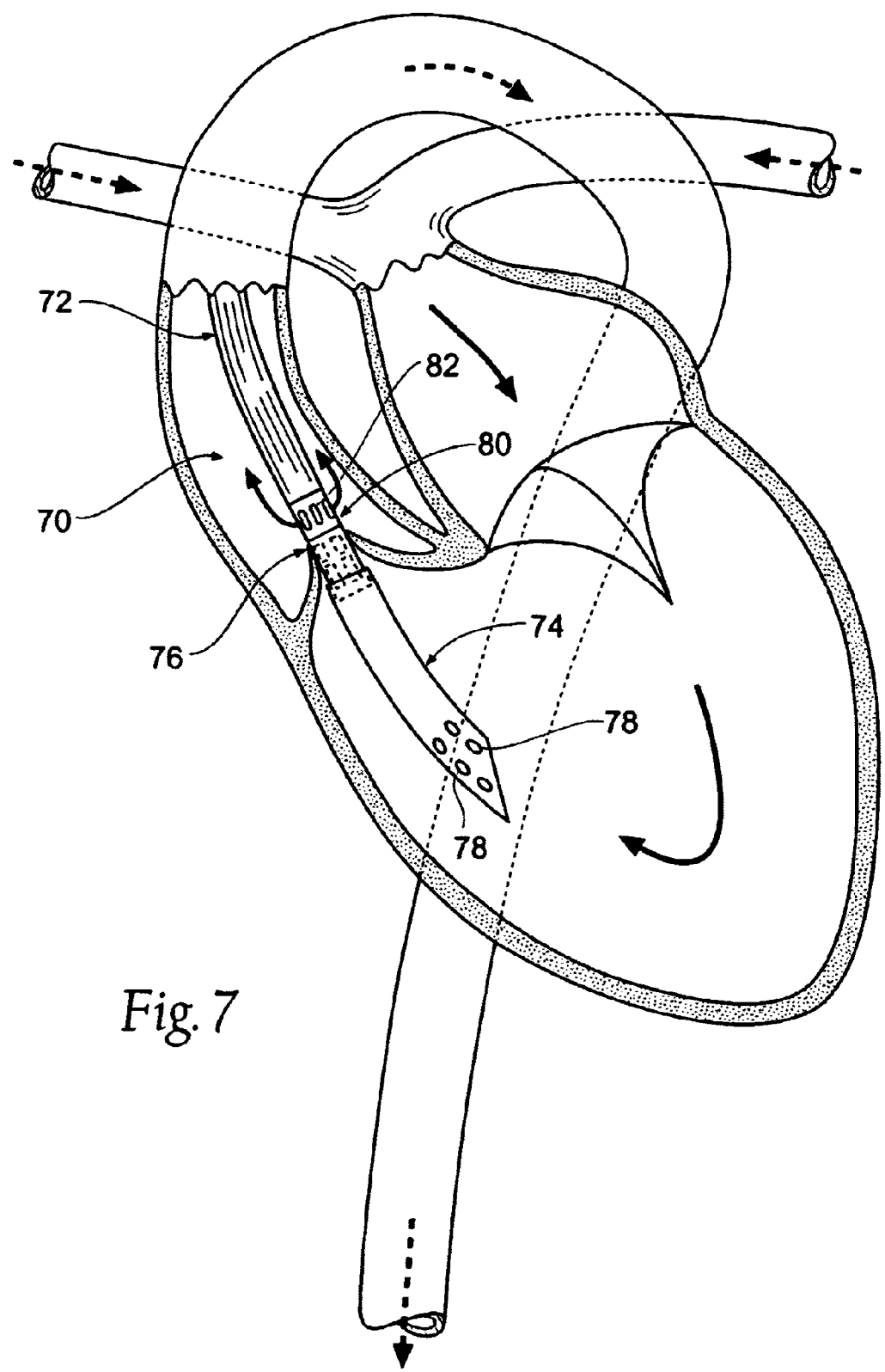
FIG. 7 is a partial cross-sectional view of a chest-cavity-space-creation device (left heart support device) provided in accordance with a fifth broad aspect of the present invention.

FIG. 7 illustrates an intravascular cannula system 70 capable of being employed to augment or replace the heart's left heart beating function during insufflation of the chest 3. The intravascular cannula system 70 is of a type similar to that shown in commonly owned and copending PCT Application No. PCT/US00/24515 entitled "Guidable Intravascular Blood Pump," the contents of which are hereby incorporated by reference. The intravascular cannula system 70 includes an elongated catheter section 72, a cannula section 74, and an intravascular blood pump 76 disposed therebetween. The cannula section 74 includes distal flow port(s) 78 and the blood pump 76 includes a shroud section 80 having a plurality of flow ports 82 formed therein. In operation, the blood pump 76 withdraws blood from the left ventricle and forcibly transports it into the aorta. This transportation of blood effectively empties or unloads the left ventricle, providing yet another space creating mechanism within the chest cavity.

It will be appreciated by those skilled in the art that changes could be made to the embodiments described above without departing from the broad inventive concepts thereof. It is understood, therefore, that this invention is not limited to the particular embodiments disclosed, but is intended to cover modifications within the spirit and scope of the present invention as defined by the appended claims.

What is claimed is:

1. A system for creating space within a patient's chest cavity to facilitate minimally invasive cardiac medical procedures, comprising:

an access conduit dimensioned to be passed through an aperture in a wall of the patient's chest and into said patient's chest cavity, said conduit having at least one insufflation lumen extending into said chest cavity and an internal lumen dimensioned to pass instruments into said chest cavity and, a seal assembly at a proximal end of said internal lumen and a sealing flange at a distal end of said internal lumen, the flange having a retracted position in which the flange is folded within the internal lumen for introduction of the access conduit into the chest cavity and an extended position in which the flange is extended from the distal end of the access conduit, an elongated member slideably advanceable through the interior lumen and including a recessed region dimensioned to receive the flange portion when folded within the internal lumen, the recessed region adapted to force the flange portion out the distal end of the internal lumen as the elongated member is advanced within the internal lumen to move the flange from the retracted position to the extended position, and an insufflation fluid source coupled to said at least one insufflation lumen for supplying insufflation fluid into said chest cavity in an amount sufficient to create space therein.

2. The system of claim 1 and further, wherein said insufflation fluid is provided having a temperature sufficiently lower than that of said patient so as to cool the organs within said chest cavity.

3. The system of claim 1 wherein the flange is biased in the extended position.

* * * * *